United States Patent
Acker et al.

[11] Patent Number: 5,935,061
[45] Date of Patent: Aug. 10, 1999

[54] OBSTETRICAL INSTRUMENT SYSTEM AND METHOD

[75] Inventors: David E. Acker, Setauket, N.Y.; Ze'Ev Weinfeld, Jerusalem, Israel

[73] Assignee: Biosense, Inc., Setauket, N.Y.

[21] Appl. No.: 09/001,844

[22] Filed: Dec. 31, 1997

Related U.S. Application Data

[60] Provisional application No. 60/034,706, Jan. 3, 1997.

[51] Int. Cl.[6] ................................................. A61B 5/103
[52] U.S. Cl. ............................ 600/304; 600/588; 600/587
[58] Field of Search .................................. 600/304, 409, 600/424, 437, 587, 588, 591

[56] References Cited

U.S. PATENT DOCUMENTS

| | | | |
|---|---|---|---|
| 2,924,220 | 2/1960 | Von Micsky | 600/591 |
| 3,913,563 | 10/1975 | Ball | 600/588 |
| 4,317,078 | 2/1982 | Weed et al. | 600/424 |
| 4,936,316 | 6/1990 | Jewett | 600/591 |
| 4,942,882 | 7/1990 | Bellinson | 600/591 |
| 5,025,787 | 6/1991 | Sutherland et al. | 128/642 |
| 5,042,486 | 8/1991 | Pfeiler et al. | 600/424 |
| 5,042,503 | 8/1991 | Torok et al. | 600/591 |
| 5,193,542 | 3/1993 | Missanelli et al. | 128/633 |
| 5,301,680 | 4/1994 | Rosenberg | 600/588 |
| 5,373,852 | 12/1994 | Harrison et al. | 600/588 |
| 5,450,857 | 9/1995 | Garfield et al. | 600/591 |
| 5,483,970 | 1/1996 | Rosenberg | 600/591 |
| 5,529,064 | 6/1996 | Rall et al. | 600/304 |
| 5,558,091 | 9/1996 | Acker et al. | 600/424 |
| 5,568,809 | 10/1996 | Ben-haim | 600/433 |
| 5,623,939 | 4/1997 | Garfield | 600/591 |
| 5,634,476 | 6/1997 | Orkin et al. | 600/588 |
| 5,729,129 | 3/1998 | Acker | 600/424 |
| 5,752,513 | 5/1998 | Acker et al. | 600/424 |
| 5,833,608 | 11/1998 | Acker | 600/409 |
| 5,840,025 | 11/1998 | Ben-haim | 600/424 |
| 5,851,188 | 12/1998 | Bullard et al. | 600/448 |
| 5,865,733 | 2/1999 | Malinouskas et al. | 600/591 |

*Primary Examiner*—Max Hindenburg
*Assistant Examiner*—Charles Marmor, II
*Attorney, Agent, or Firm*—Lerner, David, Littenberg, Krumholz & Mentlik, LLP

[57] ABSTRACT

The childbirth process is monitored by applying one or more probes to the mother and monitoring the locations of the probes by transmitting non-ionizing fields such as magnetic fields between the probes and reference elements in proximity to the mother. The magnitude and direction of movement of the probes indicates the magnitude and direction of uterine contractions. Fetal position and cervical dilation may be monitored by providing additional probes attached to the fetus and to the cervix.

31 Claims, 5 Drawing Sheets

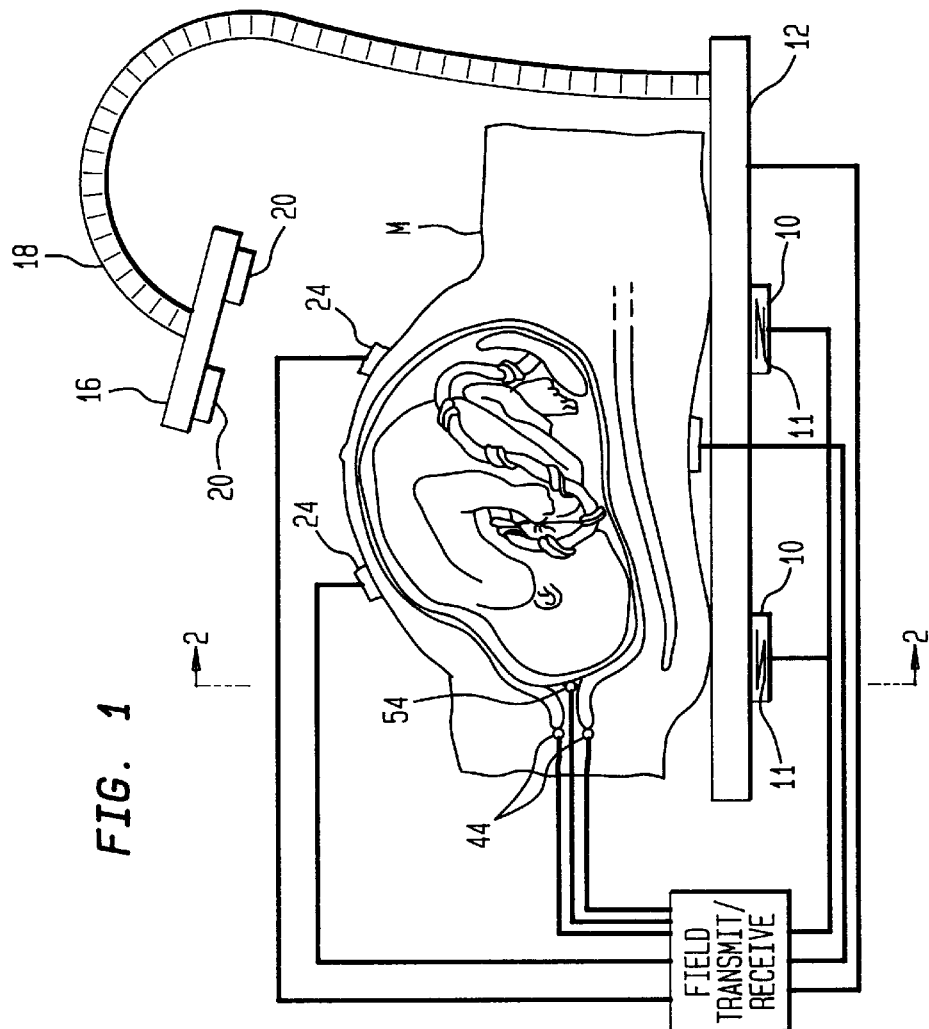
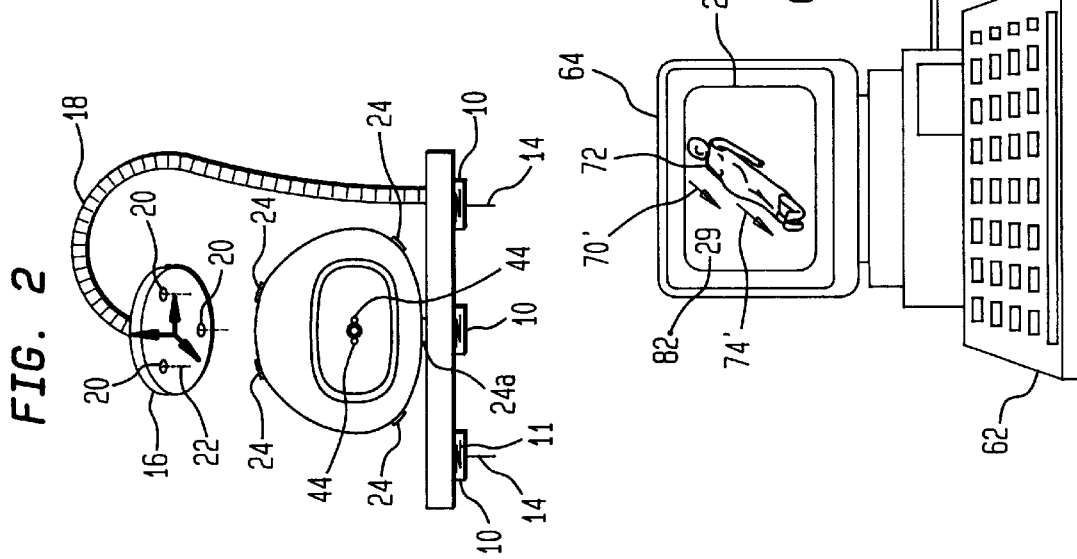
FIG. 1
FIG. 2

OBSTETRICAL INSTRUMENT SYSTEM AND METHOD

CROSS REFERENCE TO RELATED APPLICATIONS

The present application claims benefit of U.S. Provisional patent application Ser. No. 60/034,706 filed on Jun. 3, 1997, the disclosure of which is incorporated by reference herein.

FIELD OF THE INVENTION

The present invention relates to instruments and methods for monitoring the mammalian birth process.

BACKGROUND OF THE INVENTION

During childbirth, medical personnel commonly monitor the degree of dilation of the mother's cervix, the location of the fetus within the cervix and uterus and the strength and frequency of the mother's labor contractions. Much of this monitoring is conducted by direct visual observation and manual palpation. Various instruments have been proposed to aid the monitoring process. As disclosed in the U.S. Pat. No. 5,438,996, a cervimeter for monitoring the degree of cervical dilation may be based on direct mechanical measurements; or on ultrasonic measurement. In the ultrasonic cervimeter, a small ultrasonic transmitting device is attached to the mother's cervix adjacent its opening, and a small receiving device is also attached to the cervix, but on the opposite of the opening. The time of flight of ultrasonic signals between the transmitter and receiver provides an indication of the distance between them and hence an indication of the degree of cervical dilation. As disclosed in the '996 patent, and as further described in U.S. Pat. No. 3,768,459, an electromagnetic cervimeter uses an electromagnetic transmitting coil attached to one side of the cervix and an electromagnetic receiving coil attached to the opposite side. The strength of electromagnetic coupling between these coils provides an indication of the distance between the transmitter and receiver and hence an indication of cervical dilation.

As described in U.S. Pat. No. 3,913,563, the magnitude of uterine contractions can be monitored by use of a strain gauge. A flexible reed is mounted on a frame carried by the belt. The belt holds the frame against the abdominal wall. The reed extends through the frame and also contacts the abdominal wall. Contractions cause movement of the reed. The degree of movement provides an indication of the magnitude of the muscle contraction. As described in U.S. Pat. Nos. 5,634,476 and 5,218,972, pressure measuring devices bearing on the abdomen can also be used to measure changes in pressure caused by the contractions.

Other monitoring devices used in childbirth are directed to monitoring the status of the fetus during these processes. For example, a pulse monitoring device may be physically mounted on the fetus, as by mounting the pulse monitoring device to the scalp of the fetus through the cervical opening.

Despite these efforts in the art, additional improvements in monitoring the childbirth process, and in monitoring the analogous process in non-human mammalian birth would be desirable.

SUMMARY OF THE INVENTION

One aspect of the present invention provides apparatus for monitoring birth of a fetus from a mammalian mother such as a human or a non-human mammal. Apparatus according to this aspect of the invention includes one or more maternal probes and means for securing the maternal probe or probes to the body of the mother in proximity to the uterus. For example, the maternal probes may include exterior maternal probes which are to be placed on the outside of the mother's body. Alternatively or additionally, the maternal probes may include cervical probes for attachment to the cervix.

The apparatus also includes one or more reference elements with means for maintaining the reference elements in proximity to the mother's body. Preferably, the reference element or elements are placed in a location where they are substantially isolated from movement caused by the uterine contractions. For example, one or more exterior maternal probes may be mounted on the exterior of the mother's abdomen, whereas the reference element or reference elements may be secured to a part of the mother's body which is relatively isolated from the effective uterine contractions as, for example, behind the spine or on the limbs. Alternatively, one or more reference elements may be mounted on the bed supporting the mother or on a frame which can be brought into position close to the bed.

The apparatus further includes transmission means for actuating the probes and reference elements to transmit one or more non-ionizing fields such as electromagnetic or ultrasonic fields and detect the transmitted fields. Thus, each transmitted field is transmitted by one element of a transmitter-receiver pair including a reference element and a maternal probe and is detected by the other element of the pair. The apparatus most preferably further includes calculation means to determine the disposition of each maternal probe with respect to the one or more reference elements from the properties of the detected fields. As used in this disclosure, the term "disposition" includes position, orientation or both. Most preferably, the calculation means is arranged to determine at least the position of each maternal probe in a frame of reference defined by the one or more reference elements.

The calculation means desirably includes means for determining the magnitude of movement of the maternal probe or probes incident to a uterine contraction and providing a contraction signal for each maternal probe which represents the magnitude of movement of that maternal probe. Most preferably, the calculation means also include means for determining the direction of movement of each maternal probe incident to a contraction, so that the contraction signal represents the direction of movement of the maternal probe as well as its magnitude of movement. Thus, in the most preferred embodiment, the contraction signal represents the vector of movement of the maternal probe. Significant information can be obtained from a single contraction signal, from a single maternal probe. However, still further information can be obtained where plural maternal probes are used. In this case, the means for mounting the exterior maternal probes desirably is arranged to mount the probes at spaced-apart locations on the mother's body. For example, where the mounting means includes an adhesive or other mounting which secures the exterior maternal probes to the skin, the exterior maternal probes can be applied manually at the spaced-apart locations.

The calculation means is arranged to derive a separate contraction signal for each probe representing its movement and desirably is also arranged to combine the contraction signals from a plurality of the probes and provide a composite signal which represents one or more parameters of a uterine contraction. For example, a composite signal representing the magnitude of the contraction may be obtained by combining the magnitudes of movement of several maternal probes, as by summing the scalar representations of such magnitudes. A more informative composite signal may be obtained by combining the magnitudes and directions included in several contraction signals from several maternal probes as, for example, by taking the vector sum of the individual maternal probe movement vectors provide a composite contraction vector representing the magnitude and direction of movement incident to the contraction as a whole.

The ability to detect both magnitude and direction of the contractions using individual contraction signals from individual probes or using composite signals provides significant benefits. It allows the physician to detect retrograde contractions which tend to move the fetus toward the diaphragm rather than toward the cervix, or other abnormal contractions. When abnormal contractions or other abnormal conditions are detected, the physician can intervene in the delivery process, as, for example, by initiating a cesarean section. Early detection of abnormal conditions allows the physician to intervene early in a futile, abnormal labor. This minimizes unnecessary suffering of the mother and saves the fetus from the damage which could be caused by prolonged abnormal labor. It also saves the cost associated with a long, unproductive stay in the delivery room. As further discussed below, the maternal probes maybe small, unobtrusive devices. Each such maternal probe may include a small transducer arranged to detect or transmit magnetic, electromagnetic or other non-non-ionizing fields. The structure of the transducers, and those aspects of the calculation devices used to convert the properties of detected fields into disposition of the probes may be similar to those utilize heretofore in tracking the positions and orientations of intrabody probes for image-guided surgery, intrabody mapping and other procedures. Transducers and field measuring systems developed for these applications can be extremely small, on the order of a few millimeters in diameter or less and can provide continual monitoring of position and orientation with positional accuracy on the order of a few millimeters or less. These capabilities exceed those required in preferred embodiments of the present invention.

Another composite signal which may be calculated includes the magnitude and/or direction of movement of one or more -of the maternal probes relative to one or more other maternal probes. For example, where a plurality of exterior maternal probes are provided at spaced-apart locations around the circumference of the abdomen, the magnitudes of movement of the maternal probes towards one another as, for example, towards the center of the abdomen, can provide a composite indication of the magnitude of a contraction. Also, where plural maternal probes are provided at plural, axially-separated locations, spaced apart from one another in the axial or head-to-toe direction of the mother, the phase difference or time delay between contraction signals can provide information as to the manner in which the contraction propagates along the mother's body. Combinations of these approaches can also be employed.

Cervical maternal probes may be used alone or in conjunction with exterior maternal probes to obtain contraction signals as discussed above. Moreover, when a plurality of cervical maternal probes are provided, the positions of the cervical maternal probes may be compared with one another to provide the distance between the cervical maternal probes and thus provide a measure of cervical dilation.

The apparatus may further include a fetal probe and means for securing the fetal probe to the fetus. The transmission means may include means for actuating the fetal probe and one or more of the reference elements to transmit one or more additional fields between members of at least one additional transmitter-receiver pair including the fetal probe and a reference element. The calculation means may include means for determining the disposition of the fetal probe relative to the reference element. Thus, movement of the fetus can be tracked relative to the reference element. Movement of the fetal probe relative to the reference element can be taken as a direct indication of movement of the fetus through the cervix. Alternatively, the motion of the mother relative to the reference element may be canceled by subtracting the motion of one or more maternal probes relative to the reference element from the motion of one or more fetal probes relative to the reference element, to provide a representation of the fetal movement relative to the mother. Thus, in a variant of the apparatus, the fetal probe may be used without the maternal probes.

Thus, a further aspect of the invention provides a fetal probe for monitoring position of a fetus during delivery, comprising a field transducer which is adapted to detect or emit one or more non-ionizing fields and means for securing the field transducer to the fetus. Preferably, the field transducer is a magnetic field transducer adapted to detect magnetic field components in at least two different local directions relative to the probe and to provide separate data relative to each component. For example, the fetal transducer may include two or more coils or solid state sensors having non-parallel coil axes or sensing axes. The fetal probe may include a fetal heart rate monitoring transducer. The means for securing the field transducer to the fetus desirably are arranged to secure the fetal heart rate monitoring transducer to the fetus. Thus, the composite transducer including both heart rate monitoring and positional monitoring functions may be integrated as a single unit, not substantially larger than a heart rate transducer alone.

Further aspects of the invention include methods of monitoring the birth of a fetus from a mammalian mother such as a human or non-human mammal. Methods according to this aspect of the invention include the step of securing one or more maternal probes to the body of the mother in proximity to the uterus and maintaining or more reference elements in proximity to the mother's body. Methods according to this aspect of the present invention include the step of actuating the probes to transmit one or more non-ionizing fields and to detect the transmitted fields. Here again, each field is transmitted by one element of a transmitter receiver pair including a reference element and a maternal probe and detected by the other element of the pair. Methods according to this aspect of the present invention desirably also include the step of determining the disposition of each maternal probe with respect to the one or more reference elements from the properties of the detected fields. The preferred methods include the step of calculating the magnitude, direction or, most preferably, both magnitude and direction of movement of each maternal probe incident to a contraction and providing a contraction signal representing the direction, magnitude or both. The contraction signals from the individual probes may be combined to provide composite signals in the manner discussed above with reference to the apparatus. In a further embodiment of the invention, the maternal probes may include two or more maternal probes mounted to the cervix on opposite sides of the cervical opening or os. By monitoring the position of each of these maternal probes relative to the one or more reference elements, the position of the maternal probes relative to one another can be determined. This in turn provides an indication of the degree of cervical dilation. The same maternal probes may also be used in the other contraction-monitoring operations discussed above.

In a variant of the above-described methods and apparatus, both the maternal probe or probes and the reference element are secure to the mother's body in areas of the body subject to movement due to the contractions. By monitoring the disposition of the maternal probe relative to the reference element, the relative movement of these probes due to the contractions can be monitored. For example, movement of the probes towards one another can provide an indication of the magnitude of the contraction.

These and other objects, features and advantages of the present invention will be more readily apparent from the detailed description of the preferred embodiment set forth below, taken in conjunction with the accompanying drawings.

BRIEF DESCRIPTION OF THE DRAWINGS

FIG. 1 is a partially sectional, partially block diagrammatic view of apparatus in accordance with one embodiment of the invention.

FIG. 2 is a diagrammatic sectional view taken along line 2—2 in FIG. 1.

DETAILED DESCRIPTION OF THE PREFERRED EMBODIMENTS

Figure 3:
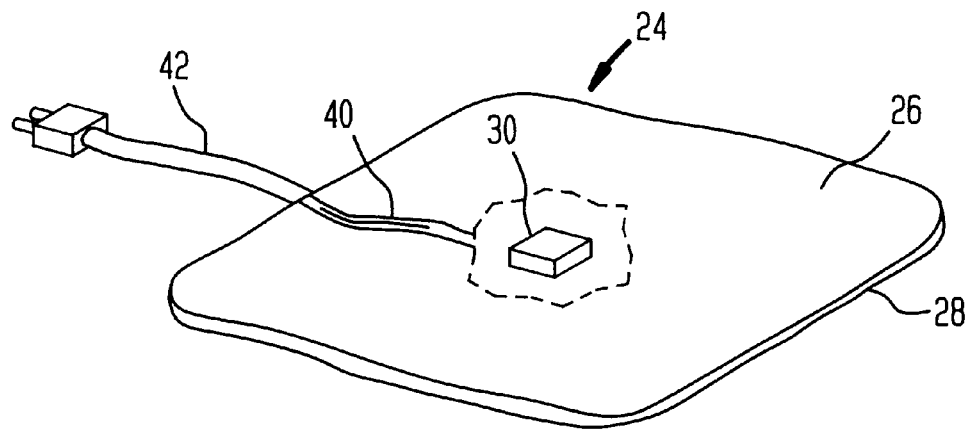
FIG. 3 is a diagrammatic perspective view of a component used in the apparatus of FIGS. 1 and 2.

Apparatus in accordance with one embodiment of the invention includes first set of reference elements 10 mounted on the underside of a patient support bed 12. Each reference element 10 includes an electrically conductive coil 11 defining a coil axis 14 concentric with the coil. These elements may be disposed in an array as disclosed, for example, in Published International Application WO 97/32179 and WO 97/29709, the disclosures of which are hereby incorporated by reference herein. For example, reference elements 10 may be disposed at corners of a triangle such that the center of the triangle is disposed beneath the abdomen of the mother when the mother lies on bed 12.

The apparatus further includes a frame 16 which is mounted to bed 12 by a deformable support 18. Support 18 may be a deformable corrugated conduit of the type commonly used to support a "goose neck" lamp. Support 18 is arranged so that frame 16 can be positioned as desired in proximity to the mother M resting on bed 12, and so that the frame will remain in a substantially constant position unless and until the frame is deliberately displaced, as by grasping it and moving it. Other suitable supports for frame 16 include arms connected to one another and connected to bed 12 by joints which are movable, but held in place by suitable detents or brakes so that the support 16 remains in place unless deliberately moved. Alternatively, frame 16 can be held on a support rigidly mounted to bed 12 or on a support which is rigidly clamped in place on the bed. Preferably, any such rigid mount is provided with a release mechanism which allows the support to be detached from the bed and moved out of the way to provide better access to the mother in the event of an emergency. A further set of reference elements 20 is mounted to frame 16. Reference elements 20, like reference elements 10, incorporate electrically conductive coils defining coil axes 22. Reference elements 20 are disposed in an array such that the coil axes 22 are non-collinear. Frame 16 and reference elements 20 may be as disclosed, for example, in commonly assigned International Publication WO 97/29683, the disclosure of which is incorporated by reference herein.

Figure 4:
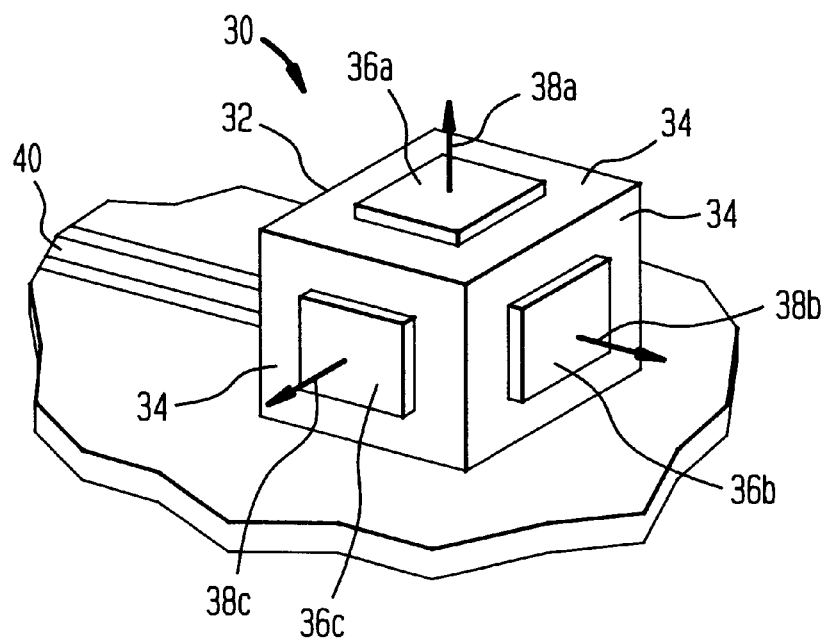
FIG. 4 is a fragmentary, diagrammatic perspective view on an enlarged scale depicting a portion of the component illustrated in FIG. 3.

The apparatus further includes a set of exterior maternal probes 24 As best seen in FIG. 3, each exterior maternal probe 24 includes a pad 26 formed from a flexible, conformable material such as a soft vinyl or other polymer of the type commonly used for self-adhesive bandages or a fabric. Pad 26 has an adhesive layer 28 on a bottom surface. A multiaxis transducer 30 is mounted on the top surface of pad 28. Transducer 30 includes a support 32 (FIG. 4) having a plurality of non-coplanar and preferably mutually orthogonal surfaces 34 and a plurality of individual sensing elements 36 mounted on the support. The sensing elements may be Hall-effect sensors, magnetoresistive sensors, magnetooptical sensors, flux gate magnetometers or other suitable sensors adapted to detect a component of a magnetic field in a particular direction and produce a component signal representing the magnitude of that magnetic field component. Thus, sensing element 36a is arranged to produce a component signal representing the magnitude of a field component in direction 38a, whereas sensing elements 36b and 36c are arranged to produce component signals representing the magnitudes of field components in directions 38b and 38c respectively. Directions 38a, 38b and 38c are in the frame of reference of support 32, and hence are local directions relative to the frame of reference of the probe. Preferably, the sensing elements are arranged to detect magnetic field components along mutually intersecting axes, or along axes which pass close to one another, so that the detected components represent components of a magnetic field at a single point or adjacent a single point. The particular arrangement depicted in FIG. 4, in which the local direction or sensing directions are orthogonal to the planes of the support, is merely illustrative. Depending upon the type of sensor, the sensing directions may be parallel to the planes of the support. However, the sensing directions desirably are orthogonal to one another. Sensor 30 may be made, for example, as described in International Publication WO 95/09562, the disclosure of which is hereby incorporated by reference herein. As set forth in the '562 published application, the sensing elements may be mounted on a flexible sheet such as a polyimide dielectric, which in turn may be deformed to fit the surfaces of the support. As also disclosed in the '562 Publication, the sensor may include one or more amplifiers for amplifying the sensor signals. Sensor 30 is connected to leads 40. Leads 40 extend along an elongated cable 42, which may be formed integrally with pad 26. The exterior maternal probes 24 are arranged to provide maximum comfort to the patient, and to withstand the conditions encountered during use in the delivery room. For example, maternal probe 24 may include a cover or encapsulant (not shown) overlying sensor 30 to protect and cushion the sensor. As described in the aforementioned 95/09562 Publication, a sensor of this type may have dimensions as small as a few millimeters or even less than one millimeter, so that the same can be incorporated in small intrabody probes, such as small catheters. Such small dimensions are desirable, but are not required in the sensors used in the exterior maternal probes. Thus, the sensor may have dimensions of a few millimeters to a centimeter and may be even larger. This permits use of larger, more economical and more robust sensing elements than can be accommodated in a sensor intended for intrabody use.

Figure 5:
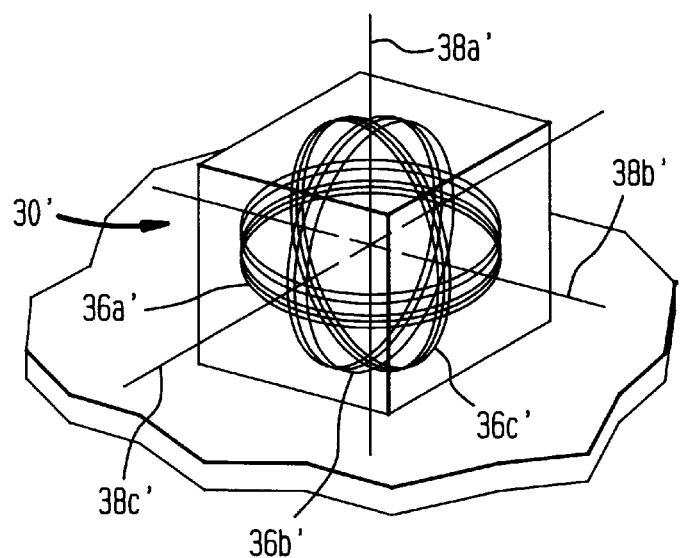
FIG. 5 is a view similar to FIG. 4 depicting a component according to a further embodiment of the invention.

In a variant, transducer 30' (FIG. 5) incorporates a set of coils 36a', 36b', 36c' wound on non-parallel axes 38a', 38b' and 38c'. Most desirably, axes 38a', 38b' and 38c' are orthogonal to one another and are mutually intersecting. Each coil is arranged to detect magnetic field components directed along its respective coil axis. Alternatively, the coils can be used as field transmitters. Once again, each coil emits a field which is directed along the associated the coil axis.

The apparatus further includes a pair of cervical maternal probes 34. Each cervical, maternal probe includes a transducer 46, which may be identical to the transducers discussed above with reference to FIGS. 4 and 5 mounted in a small housing 48. Each housing 48 is provided with a tissue anchor 50, which may be in the form of a barb, hook, grapple, or screw-like device arranged to secure the housing 48, and hence the associated transducer 46 to the tissue of the mother's uterus, adjacent the cervix C. Any other suitable form of anchoring device capable of securing the maternal cervical probes may be employed. For example, a separate elastic member or clip may be applied to hold the maternal cervical probes against the tissue. Alternatively, the housings may be provided with suturing eyelets and may be sutured in place. The maternal cervical probes are provided with cables 52. Most preferably, the maternal cervical probes and the cables are made as small as practicable.

The apparatus further includes a fetal probe 54. The fetal probe includes a clip or other securement device 56 which is arranged to secure one or more transducers 58 capable of monitoring the condition of fetus to the scalp of the fetus F during childbirth. The fetal condition monitoring transducers may include conventional elements used for the purpose of monitoring fetal heart rate, such as electrodes or photo-emitting and photodetecting devices used in a pulse oximetric scheme. The construction of fetal monitoring devices is known in the art, and any suitable set of transducers and securement devices useful in fetal monitoring by a probe attached to the fetus during childbirth may be employed as part of fetal probe 54. The fetal probe further includes a magnetic field transducer 60 similar to the field transducers discussed above. Magnetic field transducer 60 is connected to the securement device 56 so that when the fetal condition monitoring transducer 58 is secured to the fetus, the magnetic field transducer will also be secured to the fetus. A cable 62 extending from the magnetic field transducer is provided. This cable also carries signals from the fetal condition monitoring transducers 58.

The coils of reference elements 10 and 20, and the transducers incorporated in maternal probes 24 and 44, as well as the magnetic field transducer in fetal probe 54 are all connected to a field transmission and receiving device 60. The field transmitting and receiving device is arranged to convert the various component signals provided by the magnetic field transducers into digital values. The field transmitting and receiving device thus may include elements such as an analog-to-digital converters and analog or digital domain filters and multiplexing devices. The field transmission and receiving device 60 also includes digital to analog converters and output amplifiers for accepting digital information and converting the digital information into an electrical signal capable of driving the coils of reference elements 10 or 20. The field transmitting and receiving device is linked to a digital computer 62, which in turn is linked to a display device such as a conventional cathode ray tube 64. The link between the field transmitting and receiving device and the computer includes a conventional data interchange bus so that digital values of component signals from the sensing elements of the transducers can be passed to the computer, and digital values of fields to be provided by reference element coils can be passed from the computer to the field transmitting and receiving device.

Figure 6:
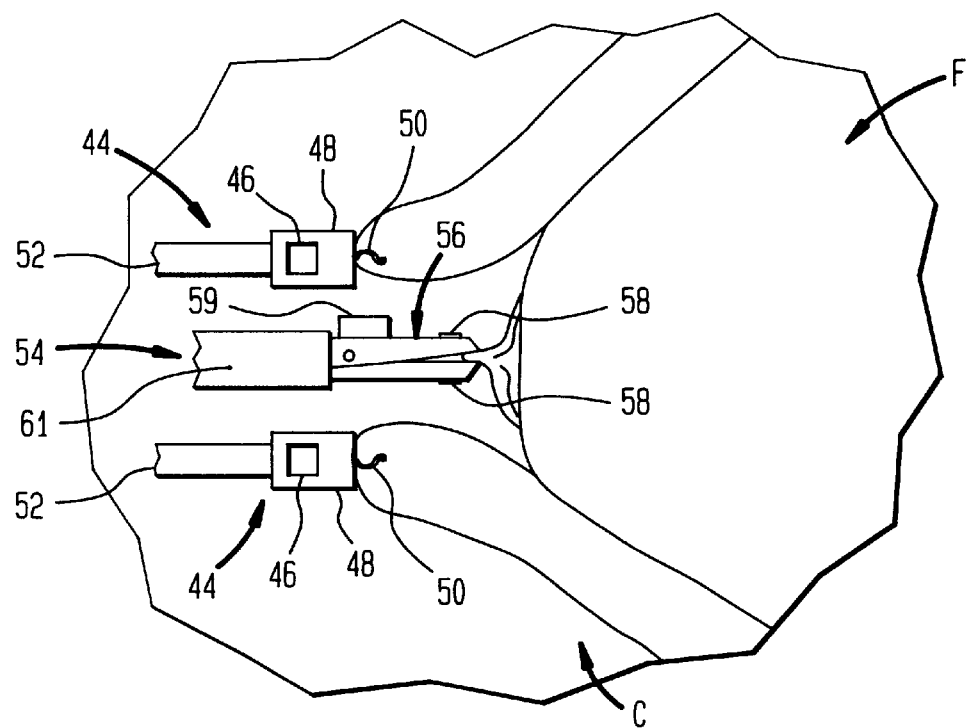
FIG. 6 is fragmentary, diagrammatic sectional view depicting portions of the apparatus illustrated in FIGS. 1 and 2.

In operation, the mother M who is about to give birth rests on table 12. The mother's pelvic region is thus in proximity to reference elements 10 beneath the table. The exterior maternal probes 24 are secured to the mother's abdomen at spaced apart locations around the periphery of her body. For example, several probes 24 may be disposed on the mother's abdominal wall, whereas one or more of the exterior maternal probes 24a may be disposed on the mother's back or on other regions of her body which are substantially isolated from local movements caused by the contractions of labor. This isolated exterior maternal probe 24a is referred to below as the principal exterior maternal probe. Cervical maternal probes 44 are applied and fastened to the uterus and fastened adjacent the cervix as depicted in FIG. 6. If the mother's amniotic sac has ruptured and that her cervix has dilated sufficiently to allow access to the fetus, fetal probe 54 is engaged with the scalp of the fetus, as also depicted in FIG. 6.

Computer 62 commands the field transmit and receive unit to actuate the coils of reference elements 10 and to receive signals from the transducers in each of the probes 24, 44 and 54. The fields emitted by coils 10 are transmitted through space and impinge on the sensors of the probes. The sensors provide signals representing the various field components at their particular locations. Computer 62 receives these signals and determines the position of each probe in the frame of reference of reference elements 10 repeatedly as new signals are acquired. Algorithms for actuating transmitting elements and deducing the position of receiving elements based on fields received from these so-actuated transmitting elements are well-known in the art of magnetic location. The various algorithms which can be used include those disclosed in the aforementioned International Publication WO 95109562; in International Publication 94/04938 and U.S. Pat. No. 5,391,199, the disclosures of which are hereby incorporated by reference herein. As disclosed in these and other publications, the fields transmitted by the coils may be direct current (steady state) fields, or alternating fields of various frequencies which are capable of passing through tissues substantially without attenuation. Also, operation of the various coils may be time-multiplexed or frequency multiplexed in known manner. The choice of particular disposition-finding algorithms, and the choice of particular coil actuation sequences, forms no part of the present invention; any suitable algorithm capable of returning accurate dispositions for the various sensors may be employed.

As the system continues to monitor the locations of the exterior maternal and fetal probes, the mother undergoes contractions of labor. These contractions cause movement of the exterior maternal transducers 24 relative to the reference elements 10. The system continually tracks the location of each exterior maternal probe 24 in the frame of reference of reference elements 10. The system continually subtracts the position of principal exterior maternal transducer 24a to provide a position of each probe 24 in the frame of reference of probe 24a. As set forth above, transducer 24a is mounted to the mother in a location on the mother's body which is substantially isolated from the maternal contractions. Thus, the subtraction operation transposes the position of probes 24 into position in a frame of reference linked to the mother, and cancels out effects caused by movement of the mother on table 12. The computer detects contractions by detecting movements of the exterior maternal transducers 24 relative to one another. For example, a movement of any single transducer 24 relative to transducer 24a exceeding a certain magnitude may be taken as a contraction. Alternatively, the system may disregard excursions having duration shorter than the minimum time normally associated with a contraction or longer than the maximum time normally associated with a contraction, or both. Alternatively or additionally, the system may disregard movements of individual transducers 24 unless such movements are associated with movements of all of the transducers, or a certain minimum number of transducers occurring within a specified time of one another.

Figure 7:
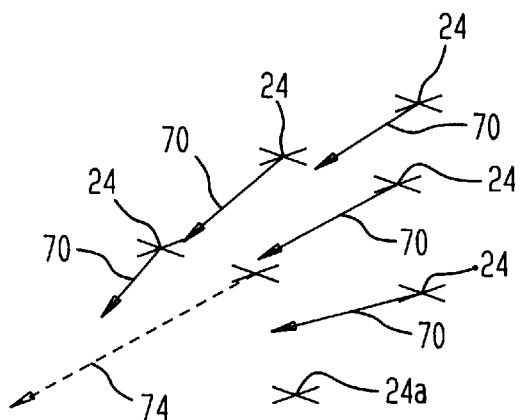
FIGS. 7 and 8 are vector diagrams depicting certain vectors determined during operation of the apparatus of FIGS. 1 and 2.

As shown in FIG. 7, the system computes a vector of motion 70 of each transducer 24, representing the excursion of such transducer from the beginning of the contraction to the maximum excursion point reached during the contraction. The system provides information to the physician via display 64 as to each of the movement vectors as, for example, a depiction of each movement vector 70' on display 64. For clarity of illustration, only one such individual vector representation 70' is shown. In practice, all of the vectors associated with the exterior maternal probes may be represented simultaneously or sequentially. The individual vectors are displayed in a frame of reference which the physician can refer conveniently to the frame of reference of the mother's body. For example, a depiction 72 of the mother may be displayed on display 64. To aid in orienting the display, the principal external transducer 24a may be provided with an external marking on its housing (not shown) which can be oriented visually to the mother's longitudinal axis when the transducer is applied to the mother's body. The transducer disposed within principal probe 24a is disposed in known orientation relative to this external marking and thus in known orientation relative to the mother's longitudinal axis. Thus, the system can calculate the orientation of each movement vector relative to the mother's longitudinal axis.

The system also calculates a composite movement vector 74 representing the vector sum of the movements of all of exterior maternal probes 24 relative to the principal maternal probe 24a. This composite vector may also be displayed as a pictorial representation 74' on display 64. Numerical representations of the vector parameters may also be displayed. Alternatively or additionally, the system may calculate the vector sum 80 of only the components of motion 76 of probes 24 in directions transverse to the longitudinal axis of the mother. A representation of this vector as well may be displayed on the display 64. This vector can be used, for example, to detect anomalous contractions involving only a part of the muscles normally involved in the contraction. Alternatively or additionally, scalar representations 82 of the magnitudes, directions or both of the various vectors discussed above may be displayed.

Figure 9:
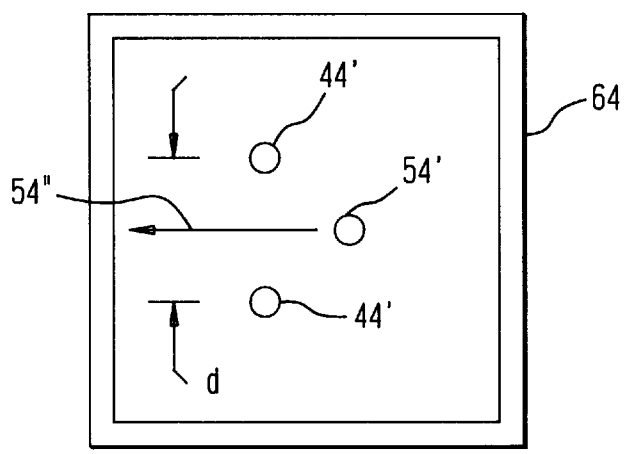
FIG. 9 is a diagrammatic view of a screen display during one mode of operation of the apparatus depicted in FIGS. 1 and 2.

The system additionally keeps track of the locations of cervical maternal probes 44 and fetal probe 54 in the frame of reference of the reference elements 10. Here again, the system may transform the locations of the probes into the frame of reference of principal maternal probe 24a, and thus into a frame of reference linked to the mother. As depicted in FIG. 9, the system desirably displays the locations of the cervical maternal probe and fetal probe together, so that their relative locations may be easily observed by medical personnel. The distance D between the cervical probes 44, as shown by schematic depictions 44' on display 64 represents the degree of cervical dilation. The position of fetal probe 54, as shown by depiction 54' relative to the cervical probes directly represents the location of the fetus relative to the cervix and hence directly represents the progress of the birth. The system may compute vectors of motion of the cervical probes and of the fetal probe. The vector of motion of fetal probe 54 represented by a vector depiction 54" on the display directly shows the motion of the fetus occasioned by a contraction. The vectors of motion of the cervical probes may be used instead of or in addition to the vectors of motion of the external probes 24 in calculating the composite direction of motion of a contraction. Alternatively or additionally, the vectors of motion of the cervical probes incident to a contraction may be displayed directly on the screen 64.

All of the information presented to the medical personnel by the system allows for enhanced monitoring of the birth process. For example, anomalous contractions, or an increase or decrease in the magnitude of contractions are readily detectable. To provide even further enhancement, the computer system may be arranged to provide pattern recognition capabilities as, for example, recognition of certain patterns of change in the composite contraction vector which indicate anomalous conditions. These patterns of change may be input directly by a physician having experience observing births and observing the patterns of change associated with normal and anomalous conditions. Alternatively, the system may incorporate "neural net" or other artificial intelligence capability for recognizing such patterns. The system may be taught in the conventional manner of programming a neural network, as by using a training set comprising the patterns of change recorded in numerous births and conditions diagnosed during such births as, for example, normal births, deviant fetal positions and retrograde contractions or other anomalous contractions.

The system discussed above can be varied by deleting some of the probes. For example, principal maternal probe 24a may be omitted, and the system may calculate the positions and movement vectors directly in the frame of reference of reference elements 10. Because the mother generally remains in place on bed 12, with only infrequent movements of her entire body, the physician can simply disregard false contraction vectors caused by body movement. Alternatively, the system can reject signals from transducers 24, 44 and 54 representing maternal movement based on the timing of such signals or based on the fact that the signals represent movement with close to rigid body correlation between movement of all of the various probes. Many of the other probes can be omitted. At the minimum, useful information can be obtained from only one exterior maternal probe and one or more reference elements. Plural reference elements 10 are not essential. As is well known in the art for magnetic location, a single multiaxis reference element, with coils arranged to emit along several mutually nonparallel axes can be used in place of plural reference elements. Alternatively, useful information can be obtained from only the fetal probe 54 and the reference element or elements. A single maternal cervical probe 44 may be employed and may be used to provide motion vector information. However, it is preferred to use a pair of maternal cervical probes to provide dilation information.

In the methods discussed above, reference elements 10 fixedly mounted to table 12 were employed, whereas reference elements 20 mounted on frame 16 were idle. However, reference elements 20 may be employed in exactly the same manner as reference elements 10. Thus, although the system is shown as including both reference elements 10 fixed to the bed and a separate set of reference elements 20 fixed to the movable frame, in practice only one of these sets would be provided. Movement of the individual probes 24, 44 and 54 may be determined by determining the position of each probe in the frame of reference of reference elements 20 and then transforming these positions into positions of the frame of reference of the principal maternal probe based upon the position and orientation of the principal probe in the frame of reference of reference elements 20. Alternatively, the position information can remain in the frame of reference of the reference elements 20. Even if the various vectors are displayed in an arbitrary frame of reference such as the frame of reference of reference elements 20, the medical personnel can observe the orientation of frame 16 and hence can mentally transpose the frame of reference of the reference elements 20 into a frame of reference relative to the mother. Alternatively, the orientations of reference elements 20 may be determined by a goniometric device which detects the orientation of frame 16 relative to table 12 or relative to a location on the mother's body mechanically or electromechanically or optically. In yet another alternative, a further reference element (not shown) may be mounted to table 12 and the position and orientation of the reference elements 20 relative to the table may be detected by detecting fields transmitted to or from such additional reference element by reference elements 20 The system can the transform the disposition of each probe into a disposition in the frame of reference of the table.

In systems according to further embodiments of the invention, one or more reference elements 104 may be mounted directly to the mother's body. For example, a reference assembly 102a bearing an array of coils or other reference element transducers 104 may be fastened to the mother M at a location on the mother's body substantially isolated from the contractions as, for example, on the mother's back. The locations of exterior maternal probes 124, fetal probe 154 and cervical probes 144 may be detected in the frame of reference defined by transducers 104 on assembly 102a in the same manner as discussed above. Here, however, because the reference elements are directly mounted to the mother, no compensation for maternal movement is necessary.

Alternatively, the reference elements may include a set of plural reference assemblies 102. Each reference assembly includes a plurality of transducers 104 and a further transducer 106. Fields can be transmitted between the further transducer 106 of each reference assembly 102 and the transducers 104 of the other reference assemblies. As described in detail in commonly assigned International Publication WO 97/29685, the disclosure of which is hereby incorporated by reference, the system can deduce the location and orientation of each reference assembly relative to the other reference assemblies from the properties of fields transmitted by transducers 106 and received by transducers 104 of the other assemblies or vice versa. This information can be used directly to provide positional information, which is continually updated as the reference assemblies move relative to one another. Thus, reference assemblies 102 serve in place of some or all of the exterior maternal transducers. Alternatively or additionally, once the positions and orientations of reference assemblies 102 are known with respect to one another, the transducers 106 of the various reference assemblies may be actuated to send or receive fields to or from additional probes 124, 144, and 154. Thus, the positions and orientations of these additional transducers in the frame of reference defined by the reference assemblies is known. In this arrangement, some of the reference elements are subject to movement caused by contractions.

Figure 10:
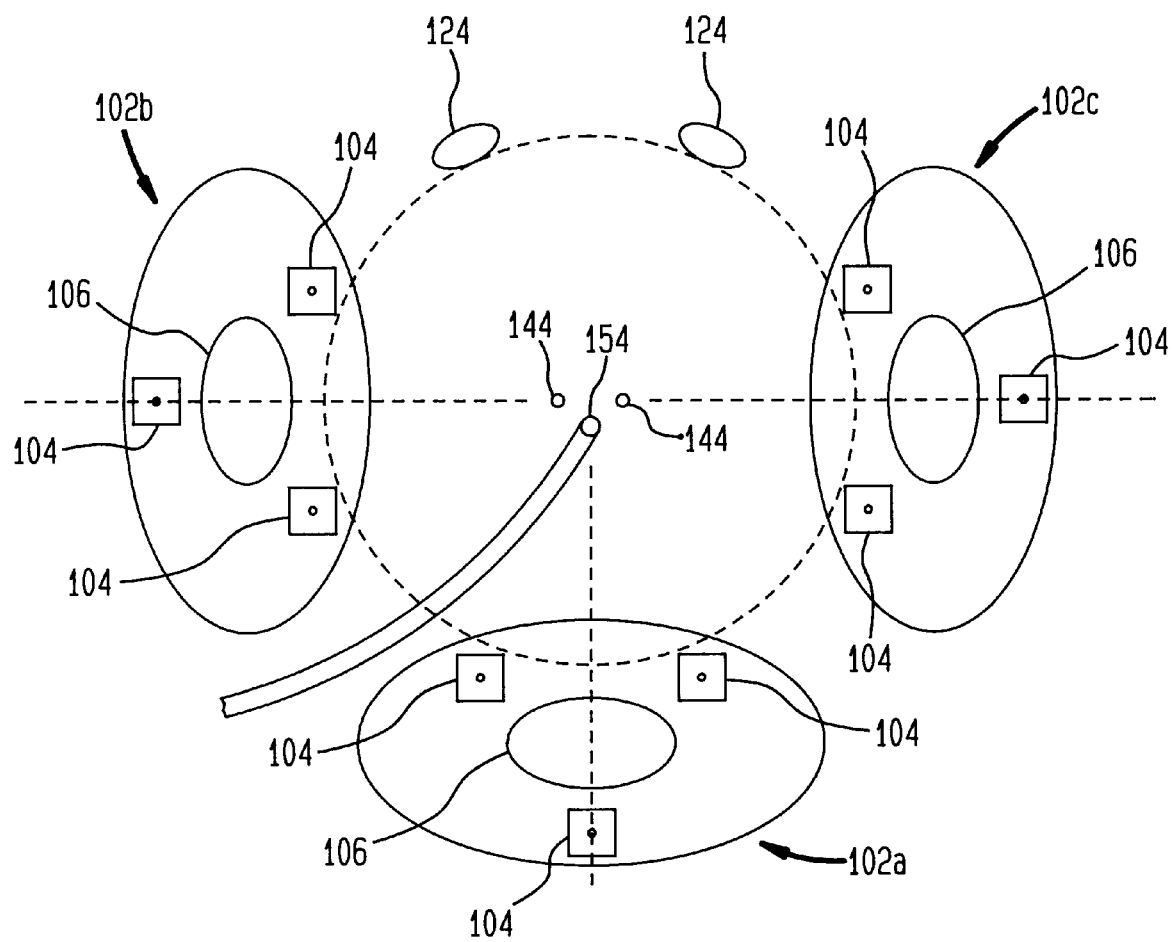
FIG. 10 is a diagrammatic view of apparatus according to a further embodiment of the invention.

The information derived by the system of FIG. 10 can be displayed in substantially the same manner as discussed above. For example, the contraction vector may be formed as a composite of the movement vectors of reference assemblies 102b and 102c with respect to reference assembly 102a together with the movement of external transducers 124 with respect to the same reference element 102a. Alternatively, the contraction vector can be calculated from the directions of movement of transducers 124 in the composite frame of reference defined by all of the transducer assemblies together.

In the systems discussed above, magnetic fields are set from the transducers associated with the reference elements and received by the transducers associated with the probes. However, the reverse arrangement can be employed. Thus, where the transducers associated with the probes are capable of transmitting fields, the transducers associated with the reference elements desirably serve as receiving transducers. The number of directions of sensitivity required in the various transducers will depend in part upon the algorithm used to detect position and/or orientation. For example, three independently located coils having axes in any known disposition other than collinear with one another provide an array of reference elements which can be used with any transducer having sensitivity in three nonparallel directions. Alternatively, where the transducer on a probe has sensitivity in only a single direction, an array of three reference element transducers, each having sensitivity in three orthogonal directions can be employed. Various combinations of numbers of axes of sensitivity in the probes, transducers and in the reference element transducers can be used in known fashion.

Also, the particular mechanical devices used to secure the various probes to the mother and fetus are merely illustrative. For example, an elastic belt or other article of clothing extending around the mother may secure the exterior maternal probes to the mother. Alternatively, the exterior maternal probes may be provided with clips or suturing eyelets for fastening to the mother's skin.

The description set forth above illustrates use of the system in conjunction with a human mother. The same system may be employed in monitoring births from other mammalian organisms. Where one or more of the reference elements is mounted to the mother, the mother may be allowed to roam and the system may operate while the mother is not in any fixed position relative to a bed or other support. For example, an animal mother may be provided with the aforementioned probes and reference elements, and the signals from such elements may be relayed by telemetry. This allows monitoring of the mother by attendants remote from the mother. Similarly, the system may be applied with telemetry to permit remote monitoring of a human mother's birth process.

As these and other variations and combinations of the features discussed above can be utilized without departing from the present invention, the foregoing description of the preferred embodiments should be taken by way of illustration rather than by way of limitation of the invention as defined by the claims.

We claim:

1. Apparatus for monitoring birth of a fetus from a mammalian mother comprising:
   (a) one or more maternal probes;
   (b) means for securing said one or more maternal probes to the body of the mother in proximity to the uterus;
   (c) one or more reference elements and means for maintaining the reference elements in proximity to the mother's body
   (d) transmission means to actuate said probes and reference elements to transmit one or more non-ionizing fields and detect the transmitted field, so that each such field is transmitted by one element of a transmitter-receiver pair including a reference element and a maternal probe, and detected by the other element of such pair; and
   (e) calculation means to determine the disposition of each maternal probe with respect to said one or more reference elements from properties of the detected fields.

2. Apparatus as claimed in claim 1 wherein said means for maintaining the reference elements in proximity to the mother's body is arrange to maintain at least one reference element substantially isolated from movement caused by uterine contractions.

3. Apparatus as claimed in claim 1 wherein said calculation means includes means for determining the magnitude of movement of at least one said maternal probe incident to a uterine contraction and providing a contraction signal for each said maternal probe representing the magnitude of movement of that maternal probe.

4. Apparatus as claimed in claim 1 wherein said calculation means includes means for determining the direction of movement of at least one said maternal probe incident to a uterine contraction and providing a contraction signal for each said maternal probe representing the direction of movement of that maternal probe.

5. Apparatus as claimed in claim 4 wherein said calculation means includes means for determining the magnitude of movement of at least one said maternal probe incident to a uterine contraction and said contraction signal for each said maternal probe so that such contraction signal is representative of the magnitude and direction of movement of that maternal probe.

6. Apparatus as claimed in claim 5 wherein said at least one maternal probe includes a plurality of probes, and wherein said means for mounting includes means for mounting said plurality of probes at spaced-apart locations on the mother's body, said calculation means including means for providing a separate contraction signal for each said probe.

7. Apparatus as claimed in claim 6 wherein said calculation means includes means for combining the contraction signals from a plurality of said transducers and providing a composite signal representing one or more parameters of a uterine contraction.

8. Apparatus as claimed in claim 7 wherein said composite signal includes data representing the magnitude of a contraction and an overall direction of movement of the contraction.

9. Apparatus as claimed in claim 1 wherein said means for mounting includes means for mounting at least some of said maternal probes on the abdominal wall of the mother.

10. Apparatus as claimed in claim 1 wherein said means for maintaining said reference elements includes means for attaching said one or more reference elements to the body of the mother in a location isolated from uterine contractions.

11. Apparatus as claimed in claim 1 wherein said means for maintaining includes means for holding said one or more reference elements in at least temporarily fixed disposition relative to a bed holding the mother.

12. Apparatus as claimed in claim 11 wherein said means for holding includes a frame holding said transducers and a support holding said frame in at least temporarily fixed disposition relative to the bed.

13. Apparatus as claimed in claim 12 wherein said support is adjustable so that the disposition of said frame relative to the bed can be altered at will.

14. Apparatus as claimed in claim 11 wherein said means for attaching includes means for fixing said reference elements to the bed.

15. Apparatus as claimed in claim 1 further comprising a fetal probe and means for securing said fetal probe to a fetus, said transmission means including means for actuating said fetal probe and said one or more reference element to transmit one or more additional fields between members of at least one transmitter-receiver pair including said fetal probe and a reference transducer, said calculation means including means for determining the disposition of said fetal probe relative to said at least one reference transducer.

16. Apparatus as claimed in claim 1 wherein said at least one maternal probe includes one or more cervical maternal probes, said means for securing including means for attaching said cervical maternal probes to the cervix of the mother.

17. Apparatus as claimed in claim 16 wherein said one or more cervical maternal probes include two or more cervical maternal probes, and wherein said calculation means includes means for calculating the distance between said cervical maternal probes.

18. A method of monitoring birth of a fetus from a mammalian mother comprising the steps of:
   (a) securing one or more maternal probes to the body of the mother in proximity to the uterus;
   (b) maintaining one or more reference elements in proximity to the mother's body;
   (c) actuating said probes and reference elements to transmit one or more non-ionizing fields and detect the transmitted fields, so that each such field is transmitted by one element of a transmitter-receiver pair including a reference element and a maternal probe, and detected by the other element of such pair; and
   (d) determining the disposition of each maternal probe with respect to said one or more reference elements from properties of the detected fields.

19. A method as claimed in claim 18 wherein at least one said reference element is maintained substantially isolated from movement caused by uterine contractions.

20. A method as claimed in claim 18 further including the steps of calculating the magnitude of movement of at least one said maternal probe incident to a uterine contraction and providing a contraction signal for each said maternal probe representing the magnitude of movement of that maternal probe.

21. A method as claimed in claim 18 further including the steps of calculating the direction of movement of at least one said maternal probe incident to a uterine contraction and providing a contraction signal for each said maternal probe representing the direction of movement of that maternal probe.

22. Apparatus as claimed in claim 21 wherein said calculating step includes calculating the magnitude of movement of at least one said maternal probe incident to a uterine contraction and said step of providing the contraction signal for each said maternal probe is performed so that such contraction signal is representative of the magnitude and direction of movement of that maternal probe.

23. A method as claimed in claim 22 wherein said step of mounting said one or more maternal probes includes the step of mounting a plurality of maternal probes at spaced-apart locations on the mother's body, said calculating step being performed so as to providing a separate contraction signal for each said probe.

24. A method as claimed in claim 23 further comprising the step of combining the contraction signals from a plurality of said transducers and providing a composite signal representing one or more parameters of a uterine contraction.

25. A method as claimed in claim 24 wherein said composite signal includes data representing the magnitude of a contraction.

26. A method as claimed in claim 24 wherein said composite signal includes data representing a direction of movement of the contraction as a whole.

27. A method as claimed in claim 23 wherein said plurality of maternal probes include a plurality of cervical maternal probes, the method further comprising the step of calculating the distance between said cervical maternal probes as a measure of uterine dilation.

28. Apparatus for monitoring birth of a fetus from a mammalian mother comprising:

(a) one or more fetal probes;

(b) means for securing said fetal probes to the body of the fetus;

(c) one or more reference elements and means for maintaining the reference elements in proximity to the mother;

(d) transmission means to actuate said probes to transmit one or more non-ionizing fields and detect the transmitted field, so that each such field is transmitted by one element of a transmitter-receiver pair including a reference element and a fetal probe, and detected by the other element of such pair; and (e) calculation means to determine the disposition of each fetal probe with respect to said one or more reference elements from properties of the detected fields.

29. Apparatus as claimed in claim 28 wherein said means for maintaining the reference elements in proximity to the mother includes means for securing the reference elements to the mother's body.

30. Apparatus as claimed in claim 28 further comprising one or more maternal probes and means for securing said one or more maternal probes to the mother, said transmission means including means for actuating said maternal probes and said one or more reference element to transmit one or more additional fields between members of at least one additional transmitter-receiver pair each such additional pair including one or more of said maternal probes and one or more of said reference transducers, said calculation means including means for determining the disposition of said maternal probes relative to said at least one reference transducer and determining position of the fetus relative to the mother based upon the positions of the fetal probes and maternal probes relative to the reference elements.

31. A method of monitoring birth of a fetus from a mammalian mother comprising:

(a) securing one or more fetal probes to the body of the fetus;

(b) maintaining one or more reference elements in proximity to the mother;

(c) actuating said probes to transmit one or more non-ionizing fields and detect the transmitted fields, so that each such field is transmitted by one element of a transmitter-receiver pair -including a reference element and a fetal probe, and detected by the other element of such pair; and (d) determining the disposition of each fetal probe with respect to said one or more reference elements from properties of the detected fields.

* * * * *

UNITED STATES PATENT AND TRADEMARK OFFICE
CERTIFICATE OF CORRECTION

PATENT NO. : 5,935,061

DATED : August 10, 1999

INVENTOR(S) : Acker, et. al.

Figure 8:
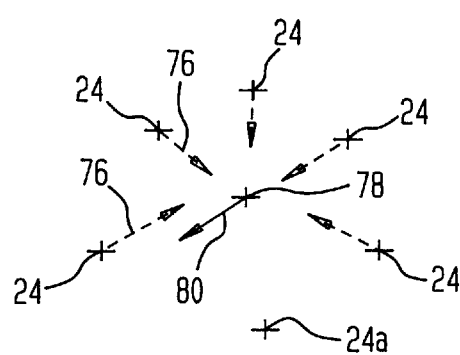

It is certified that error appears in the above-identified patent and that said Letters Patent is hereby corrected as shown below:

Column 3, line 30, "utilize" should read - - utilized - - .
Column 3, line 42, "more-of" should read - - more of - - .
Column 6, line 25, "28." should read - - 26. - -.
Column 7, line 21, "34." should read - - 44. - - .
Column 7, line 50, "60" should read - - 59 - - .
Column 7, line 51, "60" should read - - 59 - - .
Column 7, line 55, "62" should read - - 61 - - .
Column 8, line 48, "95109562" should read - - 95/09562 - - .
Column 9, line 56, after "axis", insert - - 78 - - .
Column 9, line 57, after "mother", insert - - as depicted in Fig. 8 - -.
Column 13, line 10, "to actuate" should read - - for actuating - - .
Column 13, Line 12, after "and", insert - - to - - .
Column 13, line 17, "to determine" should read - - for determining - -.
Column 13, line 22, "arrange" should read - - arranged - - .
Column 13, line 52, "transducers" should read - - probes - - .

UNITED STATES PATENT AND TRADEMARK OFFICE
CERTIFICATE OF CORRECTION

PATENT NO.    :   5,935,061
DATED         :   August 10, 1999
INVENTOR(S)   :   Acker, et. al.

It is certified that error appears in the above-identified patent and that said Letters Patent is hereby corrected as shown below:

Column 14, line 4, "transducers" should read - - reference elements - - .
Column 14, line 19, "transducer" should read - - element - - .
Column 14, line 21, "transducer" should read - - element - - .
Column 14, line 61, "Apparatus" should read - - A method - - .
Column 15, line 9, "transducers" should read - - probes - - .
Column 16, line 12, "element" should read - - elements - - .
Column 16, line 14, "pair each " should read - - pair, each - - .
Column 16, line 16, "transducers" should read - - elements - -.
Column 16, line 19, "transducer" should read - - element - - .
Column 16, line 31, "pair-including" should read - - pair including -- .

Signed and Sealed this

Seventh Day of March, 2000

Attest:

Attesting Officer

Q. TODD DICKINSON
Commissioner of Patents and Trademarks